United States Patent
Guimont et al.

(10) Patent No.: US 9,636,293 B2
(45) Date of Patent: *May 2, 2017

(54) LATEX NAIL COMPOSITIONS HAVING LOW AMOUNTS OF PHOTO-INITIATOR

(71) Applicant: L'ORÉAL, Paris (FR)

(72) Inventors: Aline Aude Guimont, Westfield, NJ (US); Chunhua Li, Hillsborough, NJ (US); Xianzhi Zhou, Millburn, NJ (US); Hy Si Bui, Piscataway, NJ (US); Jean-Thierry Simonnet, Rueil Malmaison (FR)

(73) Assignee: L'ORÉAL, Paris (FR)

( * ) Notice: Subject to any disclaimer, the term of this patent is extended or adjusted under 35 U.S.C. 154(b) by 105 days.

This patent is subject to a terminal disclaimer.

(21) Appl. No.: 14/512,995

(22) Filed: Oct. 13, 2014

(65) Prior Publication Data

US 2016/0101038 A1   Apr. 14, 2016

(51) Int. Cl.
| | | |
|---|---|---|
| *A61K 8/00* | (2006.01) | |
| *A61Q 3/02* | (2006.01) | |
| *A61K 8/87* | (2006.01) | |
| *A61K 8/81* | (2006.01) | |
| *A61K 8/55* | (2006.01) | |

(52) U.S. Cl.
CPC .................. *A61K 8/87* (2013.01); *A61K 8/55* (2013.01); *A61K 8/8141* (2013.01); *A61K 8/8152* (2013.01); *A61Q 3/02* (2013.01); *A61K 2800/42* (2013.01); *A61K 2800/43* (2013.01); *A61K 2800/54* (2013.01); *A61K 2800/594* (2013.01); *A61K 2800/81* (2013.01)

(58) Field of Classification Search
CPC ...... A61K 8/87; A61K 8/8157; A61K 8/8141; A61K 8/8152; A61K 8/55; A61Q 3/06; A61Q 3/02
See application file for complete search history.

(56) References Cited

U.S. PATENT DOCUMENTS

| | | | |
|---|---|---|---|
| 3,928,113 A * | 12/1975 | Rosenberg | A61K 8/87 132/73 |
| 4,324,744 A | 4/1982 | Lechtken et al. | |
| 4,737,593 A | 4/1988 | Ellrich et al. | |
| 5,435,994 A | 7/1995 | Valenty | |
| 5,456,905 A | 10/1995 | Valenty | |
| 5,534,559 A | 7/1996 | Leppard et al. | |
| 5,538,717 A | 7/1996 | La Poterie | |
| 5,637,292 A | 6/1997 | Thomas | |
| 5,672,647 A | 9/1997 | de La Poterie et al. | |
| 5,731,134 A | 3/1998 | Honan et al. | |
| 5,942,290 A | 8/1999 | Leppard et al. | |
| 6,011,078 A | 1/2000 | Reich et al. | |
| 6,020,528 A | 2/2000 | Leppard et al. | |
| 6,080,413 A | 6/2000 | Ellingson et al. | |
| 6,123,931 A | 9/2000 | Ellingson et al. | |
| 6,238,679 B1 * | 5/2001 | de la Poterie | A61K 8/37 424/401 |
| 6,297,950 B1 | 10/2001 | Erwin | |
| 6,306,375 B1 | 10/2001 | Ellingson et al. | |
| 6,372,201 B1 | 4/2002 | Leuridan et al. | |
| 6,391,964 B1 * | 5/2002 | Tartaglia | A61K 8/8152 206/568 |
| 6,481,444 B1 * | 11/2002 | Lilley | A45D 29/00 132/200 |
| 6,486,226 B2 | 11/2002 | Al-Akhdar et al. | |
| 6,486,228 B2 | 11/2002 | Kohler et al. | |
| 6,803,394 B2 | 10/2004 | Lilley et al. | |
| 7,037,953 B2 | 5/2006 | Chatterjee et al. | |
| 7,375,144 B2 | 5/2008 | Gilmer | |
| 7,445,770 B2 | 11/2008 | Berezkin et al. | |
| 8,088,414 B2 | 1/2012 | Siepmann et al. | |
| 8,114,938 B2 | 2/2012 | Berezkin et al. | |
| 8,263,677 B2 | 9/2012 | Conger et al. | |
| 8,367,742 B2 | 2/2013 | Vu et al. | |
| 8,399,537 B2 | 3/2013 | Conger et al. | |
| 8,492,454 B2 | 7/2013 | Vu et al. | |
| 8,541,482 B2 | 9/2013 | Vu et al. | |
| 8,846,011 B2 | 9/2014 | Kojima et al. | |
| 2008/0081054 A1 | 4/2008 | Ilekti | |
| 2010/0088776 A1 | 4/2010 | Bauer et al. | |
| 2010/0160475 A1 | 6/2010 | Stizmann et al. | |
| 2011/0060065 A1 | 3/2011 | Vu et al. | |
| 2011/0081306 A1 | 4/2011 | Vu et al. | |
| 2011/0082228 A1 | 4/2011 | Vu | |
| 2011/0182838 A1 | 7/2011 | Vu et al. | |
| 2011/0274633 A1 | 11/2011 | Vu et al. | |
| 2012/0199151 A1 | 8/2012 | Haile | |
| 2012/0276028 A1 | 11/2012 | Kojima et al. | |
| 2013/0034512 A1 | 2/2013 | Kozacheck et al. | |
| 2013/0078207 A1 | 3/2013 | Sanbonmatsu | |
| 2013/0199560 A1 | 8/2013 | Haile | |
| 2015/0190331 A1 * | 7/2015 | Chang | A61K 8/8152 424/61 |

FOREIGN PATENT DOCUMENTS

| | | |
|---|---|---|
| JP | 2011020956 A | 2/2011 |
| WO | 2012/163851 A2 | 12/2012 |

(Continued)

OTHER PUBLICATIONS

DSM Bright Science, Brighter Living, Product Data Sheet, NeoRad R-452, Sep. 13, Version: 030370/4.0; www.dsmcoatingresins.com.

(Continued)

*Primary Examiner* — Lakshmi Channavajjala
(74) *Attorney, Agent, or Firm* — Oblon, McClelland, Maier & Neustadt, L.L.P.

(57) ABSTRACT

A nail compositions comprising at least one photo-curable polymer dispersed in water (latex), at least one non-photo-curable polymer dispersed in water (latex), at least one photo-initiator, optionally at least one plasticizer, optionally a colorant, and water are provided. Also provided are nail composition systems and kits comprising the nail compositions of the invention together with a base coat composition and/or a top coat composition.

17 Claims, No Drawings

(56) References Cited

FOREIGN PATENT DOCUMENTS

| WO | 2014/028021 A1 | 2/2014 |
| WO | 2014/033656 A1 | 3/2014 |
| WO | 2014/088570 A1 | 6/2014 |

OTHER PUBLICATIONS

DSM, Safety Data Sheet, NeoRad R-452.
DSM Bright Science, Brighter Living, Product Data Sheet, NeoRad R-465, Sep. 13, Version: 030842/5.0; www.dsmcoatingresins.com.
DSM, Safety Data Sheet, NeoRad R-465.
U.S. Appl. No. 14/513,011, filed Oct. 13, 2014, Guimont et al.
U.S. Appl. No. 14/513,023, filed Oct. 13, 2014, Guimont et al.

* cited by examiner

LATEX NAIL COMPOSITIONS HAVING LOW AMOUNTS OF PHOTO-INITIATOR

FIELD OF THE INVENTION

The present invention relates to photo-curable nail compositions for coating natural or artificial nails. The compositions comprise low amounts of photo-initiators and are water based rendering them safer to the user and the environment.

DISCUSSION OF THE BACKGROUND

UV (ultraviolet) curable nail polish (including nail gel) compositions are discussed, for example, in U.S. Pat. Nos. 5,435,994 and 5,456,905, and US patent application publication nos. 2011/082228, 2011/081306, 2011/060065, 2011/182838 and 2011/274633. UV gel compositions typically consist of a layer of basecoat for adhesion on the nails, two color coats to enhance the color, and one top coat for shine. Each coating typically needs to be cured with a UV Lamp or UV LED. A UV gel system or kit typically includes a base coat composition, a color coat composition and a top coat composition.

Currently commercially available UV gels are organic solvent-based and utilize high amounts (high load) of UV curable monomer/oligomer resins as well as high loads of photo-initiators. See, for example, US 2012/199151, US 2013/034512, and U.S. Pat. No. 8,541,482. These monomer/oligomer resins and photo-initiators may cause sensitization/irritation to the nails and hands, and thus pose a safety concern to consumers. In addition, the solvents used can be damaging to the environment and thus pose also an environmental concern.

The adhesion to the nail and the cohesion among the layers of the currently available UV gel composition(s) is often very strong and difficult to remove from nails. To remove such UV gel products from nails, it is usually required to soak nails with a harsh solvent such as acetone for 10 minutes or more to effect removal. Frequent and/or prolonged use of such removal solvents in this manner can damage nails such as, for example, by making them dry and brittle. At the same time, the removal process can be time-consuming.

To overcome some of the disadvantages of the above-described solvent-based nail systems, aqueous UV-curable nail compositions have been investigated, for example, in US2012/0276028. This disclosure exemplifies high amounts of UV-curable polymer (greater than 90%). Currently, there still are no commercially-available aqueous photo-curable nail-covering products.

There remains a need for photo-curable compositions for application to nails, such as for coloring nails, that afford good wear properties, such as good adherence to nails, with less damage to the nails and the use of which is safer for the consumer and the environment.

SUMMARY OF THE INVENTION

The present invention provides a water-based composition for application to the nails that comprises (a) from about 6% to about 20%, by dry polymer weight, of at least one photo-curable polymer dispersed in water; (b) equal to or greater than about 10%, by dry polymer weight, of at least one non-photo-curable polymer dispersed in water; (c) less than or equal to about 2% of at least one photo-initiator; (d) optionally at least one plasticizer; (e) optionally a colorant; and (f) water; wherein the ratio, by dry polymer weight, of the at least one photo-curable polymer (a) to the at least one non-photo-curable polymer (b) is from about 4:1 to about 1:5, and the sum, by dry polymer weight percent, of the photo-curable polymer (a) plus the non-photo-curable polymer (b) is from about 25% to about 40%; all weights being relative the total weight of the composition.

The present invention also provides a water-based composition for application to the nails that comprises (a) from about 6% to about 20%, by dry polymer weight, of at least one photo-curable polymer dispersed in water; (b) equal to or greater than about 10%, by dry polymer weight, of at least one non-photo-curable polymer dispersed in water, said non-photo-curable polymer having a low Tg; (c) less than or equal to about 2% of at least one photo-initiator; (d) is free of plasticizer; (e) optionally a colorant; and (f) water; wherein the ratio, by dry polymer weight percent, of the at least on photo-curable polymer (a) to the at least one non-photo-curable polymer (b) is from about 4:1 to about 5:1; all weights being relative the total weight of the composition.

The compositions of the invention are water based (aqueous), not solvent based, and require substantially less photo-initiator than conventional UV-curable nail gel compositions (which typically contain about 4% initiators). The polymers in the current compositions are dispersed in water and are commonly referred to as "latexes." Being water based, the current compositions are less irritating than conventional UV-curable nail gels. The instant compositions afford high adhesion to nails and yet are easy to remove.

The compositions of the invention can be used as a color coat to be used alone or in a system for treating and/or coloring nails. When used alone, the compositions preferably are applied as two coats. A coat may include one or more layers.

The present invention also provides a nail treating or coloring system comprising (1) a base coat composition comprising at least one water-dispersed polymer and optionally a plasticizer; (2) a color coat composition comprising from about 6% to about 20%, by dry polymer weight, of at least one photo-curable polymer dispersed in water, equal to or greater than about 10%, by dry polymer weight, of at least one non-photo-curable polymer dispersed in water, equal to or less than about 2% of at least one photo-initiator, optionally at least one plasticizer, optionally a colorant, and water; and (3) a topcoat composition comprising at least one water-dispersed polymer, and optionally a plasticizer.

The present invention further relates to methods for making up, treating and/or protecting nails comprising applying to the nails a composition according to the invention.

The present invention also relates to a kit for a nail composition system, said kit comprising (1) a base coat composition comprising a water-dispersed polymer and (2) a color coat composition according to the invention.

It is to be understood that both the foregoing general description and the following detailed description are exemplary and explanatory only, and are not restrictive of the invention.

DETAILED DESCRIPTION OF THE INVENTION

The compositions of the invention may be clear, but preferably are colored. These compositions are particularly useful as color coats for application to nails. Unlike conventional UV-curable nail gels used in color coat compositions, the current compositions are water-based not organic solvent-based. The current compositions utilize at least one photo-curable latex film former. The photo-curable latexes used in the current compositions are already pre-polymerized prior to inclusion in the current composition. As a result, the current compositions utilize significantly lower levels of photo-initiators than conventional UV-curable gels. The current compositions are thus safer to the user and the environment than conventional UV nail gels. Surprisingly, even while using milder and more eco-friendly components, the current compositions still afford higher adhesion and easier removal than conventional UV-curable nail gels, even when used as color coats.

Not to be bound by theory, it is surmised the photo-curable latex enables the formation of a 3-D network yielding a film with some rigidity thereby enhancing wear as well as affording water resistance. The non-photo-curable latex contributes flexibility to the resulting films preventing chipping, imparting resistance and also enhancing adhesion to the nail or to another coat.

The compositions of the invention preferably are free of organic solvents.

When the non-photo-curable latex in the instant compositions is a low Tg latex, the composition may omit a plasticizer.

The compositions of the invention may be used alone or in combination with base and/or top coats. Surprisingly, even when the compositions of the invention are used alone they afford smooth nail color coats that are long lasting and yet easier to remove than traditional UV-curable nail gel compositions. As these compositions may practically be used alone, the compositions of the invention provide a simplified, one-composition application routine. When used alone as a color coat, the compositions of the invention are typically applied as a double coat.

Other than in the operating examples, or where otherwise indicated, all numbers expressing quantities of ingredients and/or reaction conditions are to be understood as being modified in all instances by the term "about."

As used herein, the following terms have the following meanings.

"About" means within 10% of the indicated number. Thus, "about 10%" means 9% to 11%, and "about 2%" means 1.8% to 2.2%.

"At least one" means one or more and thus includes individual components as well as mixtures/combinations.

"Adhesion" refers to chemical or physical bonding between a coating (e.g. a nail polish) and a substrate (e.g. a nail surface or a base coat). Good adhesion between nail polish and nail surface should translate to good wear properties on consumers. Adhesion properties can be quantified by in-vitro methods such as a cross-cut adhesion test. In the test, a lattice pattern is cut into the coating and penetrates through to the substrate. A pressure sensitive tape is applied to the sample and then pulled off. The adhesion property can be quantified by the area of the coating remaining after peeling. For example, if the whole film remains after peeling, it indicates excellent adhesion. If most of the film gets peeled off, it indicates poor adhesion. The cross-cut test is a recognized industrial standard test for measuring adhesion of coatings. (Reference # ISO/DIN 2409, ASTM D3359).

"Comprising" means that other ingredients and/or steps that do not affect the end result may be added. The products, compositions, methods and processes of the present invention can include all the essential elements and limitations of the invention described herein as well as any of the additional or optional ingredients, components, steps, or limitations described herein.

"Film former" or "film forming agent" means a polymer or resin that leaves a film on the substrate to which it is applied, for example, after a solvent accompanying the film former has evaporated, absorbed into and/or dissipated on the substrate. In the context of this application, the photo-curable and non-photo-curable polymers (and consequently the latex dispersions of said polymers) are film formers.

"Free" or "devoid" of as it is used herein means that while it is preferred that no amount of the specific component be present in the composition, it is possible to have very small amounts of it in the compositions of the invention provided that these amounts do not materially affect at least one, preferably most, of the advantageous properties of the compositions of the invention. Thus, for example, "free of solvents" means that non-aqueous solvents are preferably omitted (that is 0% by weight), but can be present in the composition at an amount of less than about 0.25% by weight, typically less than about 0.1% by weight, typically less than about 0.05% by weight, based on the total weight of the composition as a whole.

The term "glass transition temperature" (Tg) generally refers to the temperature at which amorphous material changes from a glassy solid state to a rubbery state. The temperature may be measured by standard techniques in the art, such a Differential Scanning calorimetry (DSM), e.g., according to a standard protocol such as ASTM D3418-97 standard.

"Low Tg" or "Low Glass Transition Temperature," such as "latex with at least one low Tg" or "polymer with at least one low Tg" as used herein means the latex, when dried, or the polymer has at least one glass transition temperature (Tg) at or below room temperature (25° C.). Some film forming polymers yield films having more than one Tg. For purposes of this application, said film forming polymer has a "low Tg" if at least one of its Tgs is at or below 25° C.

"INCI" is an abbreviation of International Nomenclature of Cosmetic Ingredients, which is a system of names provided by the International Nomenclature Committee of the Personal Care Products Council to describe personal care ingredients.

"Nails" mean finger and toes nails, natural or synthetic.

"Photo-curable" or "photo-crosslinkable" are terms known to one skilled in the art of nail polishes. See, e.g. US2012/0276028 and U.S. Pat. No. 7,375,144. When referring to a polymer it means the polymer is cross-linked ("cured") when exposed to active energy radiation, for example UV light, or even visible light, resulting in generally cross-linked polymeric networks. Photo-curing of a polymer yields a tougher film that typically is resistant to the elements, such as water, and adheres better to a substrate, such as nails.

"Polymers" as defined herein, include homopolymers and copolymers formed from at least two different types of monomers.

"Solids content" or "dry weight" as used herein refers to the weight of a polymer that has been dispersed in a liquid, for example in water. It is the weight of the polymer either before it is dispersed in the water or after water is evaporated from the latex dispersion.

"Substituted" as used herein, means comprising at least one substituent. Non-limiting examples of substituents for substitution include atoms, such as oxygen atoms and nitrogen atoms, as well as functional groups, such as hydroxyl groups, ether groups, alkoxy groups, acyloxyalky groups, oxyalkylene groups, polyoxyalkylene groups, carboxylic acid groups, amine groups, acylamino groups, amide groups, halogen-containing groups, ester groups, thiol groups, sulphonate groups, thiosulphate groups, siloxane groups, and polysiloxane groups. The substituent(s) may be further substituted.

"Tackiness" as used herein refers to the sticky feeling on the surface of a nail that has been treated with a nail composition, such as nail polish. It is measured by how much a cotton-tipped swab, e.g. a Q-Tip™, sticks to the surface of the treated nail when the Q-Tip is rubbed across the nail. Specifically, the tackier the nail surface is the more cotton fibers that are pulled from the Q-Tip and deposited on the nail surface when the Q-Tip is rubbed across the nail.

The "wear" of compositions as used herein, refers to the extent by which the color of the composition remains the same or substantially the same as at the time of application, as viewed by the naked eye, after a certain period or an extended period of time. Wear properties may be evaluated by any method known in the art for evaluating such properties. For example, wear may be evaluated by a test involving the application of a composition to nails (human or synthetic) and evaluating the color of the composition after an extended period of time. For example, the color of a composition may be evaluated immediately following application to nails and these characteristics may then be re-evaluated and compared after a certain amount of time. Further, these characteristics may be evaluated with respect to other compositions, such as commercially available compositions.

The compositions and methods of the present invention can comprise, consist of, or consist essentially of the essential elements and limitations of the invention described herein, as well as any additional or optional ingredients, components, or limitations described herein or otherwise useful.

All percentages, parts and ratios herein are based upon the total weight of the compositions of the present invention, unless otherwise indicated.

As used herein, all ranges provided are meant to include every specific range within, and combination of subranges between, the given ranges. Thus, a range from 1-5, includes specifically 1, 2, 3, 4 and 5, as well as subranges such as 2-5, 3-5, 2-3, 2-4, 1-4, etc As used herein a range of ratios is meant to include every specific ratio within, and combination of subranges between, the given ranges.

The present invention provides a composition for application to the nails that comprises:
- (a) from about 6% to about 20%, by dry weight, of at least one photo-curable polymer dispersed in water;
- (b) equal to or greather than about 10%, by dry weight, of at least one non-photo-curable polymer dispersed in water;
- (c) less than or equal to about 2% by weight of at least one photo-initiator;
- (d) from about 0% to about 8% by weight of at least one plasticizer;
- (e) optionally a colorant; and
- (f) from about 40% to about 70% water;
wherein the ratio, by dry polymer weight, of the at least one photo-curable polymer (a) to the at least one non-photo-curable polymer (b) is from about 4:1 to about 1:5, and the sum, by dry polymer weight percent, of the photo-curable polymer (a) plus the non-photo-curable polymer (b) is from about 25% to about 40%; all weights being relative the total weight of the composition.

In another embodiment, the present invention provides a composition for application to the nails that comprises:
- (a) from about 6% to about 20%, by dry weight, of at least one photo-curable polymer that is dispersed in water, said polymer being selected from acrylated polyurethane;
- (b) from about 10% to about 30%, by dry weight, of a non-photo-curable polymer that is dispersed in water, said polymer being selected from polyurethanes, styrene acrylic copolymers, and mixtures thereof;
- (c) from about 0.5% to about 2% by weight of at least one photo-initiator having at least one wavelength greater than about 200 nm;
- (d) from about 0% to about 8% by weight of a plasticizer selected from tributyl citrate, dipropylene glycol dibenzoate, and mixtures thereof;
- (e) from about 0.01% to about 10% by weight a colorant; and
- (f) from about 40% to about 70% water;
wherein the ratio, by dry polymer weight, of the at least one photo-curable polymer (a) to the at least one non-photo-curable polymer (b) is from about 4:1 to about 1:5, and the sum, by dry polymer weight percent, of the photo-curable polymer (a) plus the non-photo-curable polymer (b) is from about 25% to about 40%; all weights being relative the total weight of the composition.

In an embodiment the compositions of the invention may include two non-photo-curable polymers, each of which is dispersed in water, one such polymer having a low Tg, the second polymer having a Tg higher than the first polymer, said compositions also comprising at least one plasticizer.

In another embodiment the compositions of the invention may include at least one second plasticizer that is different from the first plasticizer.

In another embodiment the present invention provides a composition for application to the nails comprising:
- (a) from about 6% to about 20%, by dry weight, of at least one photo-curable polymer dispersed in water;
- (b) equal to greater than about 10%, by dry weight, of at least one non-photo-curable polymer having at least one low Tg, said polymer being dispersed in water;
- (c) less than or equal to about 2% by weight of at least one photo-initiator;
- (d) about 0% plasticizer;
- (e) optionally a colorant; and
- (f) from about 40% to about 70% water;
wherein the ratio, by dry polymer weight, of the at least one photo-curable polymer (a) to the at least one non-photo-curable polymer (b) is from about 4:1 to about 1:5, and the sum, by dry polymer weight percent, of the photo-curable polymer (a) plus the non-photo-curable polymer (b) is from about 25% to about 40%; all weights being relative the total weight of the composition.

In an embodiment, the compositions of the invention are used as color coats for nails.

In an embodiment, the compositions of the invention are used alone and applied in two coats. When more than one coat is applied, the compositions are cured before application of the next coat.

In an embodiment the invention provides a nail treating or coloring system comprising a base coat, a color coat and a top coat as follows.

(1) At least one base coat composition. Any base coat may be used. Preferably the base coat comprises at least one polymer-in-water dispersion.

(2) At least one color coat composition comprising at least one photo-curable polymer dispersed in water; at least one non-photo-curable curable polymer dispersed in water; equal to or less than about 2% of at least one photo-initiator; optionally at least one plasticizer; optionally a colorant; and water; wherein the ratio by dry weight of the at least one photo-curable polymer to the at least one non-photo-curable polymer is from about 4:1 to about 1:5 and the sum, by dry weight percent, of the photo-curable and non-photo-curable polymers is from about 25% to about 40%.

(3) At least one top coat composition. Any top coat may be used. Preferably the topcoat comprises at least one polymer-in-water dispersion.

The at least one polymer-in-water dispersion (latex) in the at least one base coat and/or the top coat can be, independently, a photo-curable, or non-photo-curable polymer, or a mixture of both.

In another embodiment the invention provides a nail composition system comprising:

(1) at least one base coat composition comprising a polymer-in-water dispersion and at least one adhesive compound; and (2) at least one color coat composition comprising at least one photo-curable polymer dispersed in water, at least one non-photo-curable polymer having at least one low Tg and being dispersed in water, at least one plasticizer, and a colorant.

The base coat may also further comprise at least one plasticizer and/or coalescent agent. The polymer-in water dispersion of the base coat may be photo-curable or non-photo-curable, or a mixture of both.

The foregoing nail composition and nail system embodiments may be visualized as follows:

| |
|---|
| Top Coat (Optional) |
| Color Coat |
| Color Coat |
| Base Coat (Optional) |
| Nail |

As depicted in the above table, preferably 2 color coats (consisting of the inventive compositions) are used. A clear basecoat and/or topcoat can optionally be used as well. The basecoat can be used to improve the adhesion of the nail polish on nail surface and, thus, the wear of the product. The topcoat can improve shine of the product. Each coat needs to be fully dried before applying another coat on top of it.

In another embodiment the present invention provides a method of making up, treating and/or protecting nails comprising applying to the nails a composition according to the invention.

In another embodiment the invention provides a method of making up, treating and/or protecting nails comprising applying to the nails (1) at least one base coat composition comprising a polymer dispersed in water, (2) at least one color coat comprising at least one photo-curable polymer dispersed in water, and (3) optionally a topcoat comprising a polymer dispersed in water.

In another embodiment the invention provides a method of removing nail covering compositions that comprise (1) at least one base coat composition comprising a polymer dispersed in water, and (2) at least one color coat comprising a photo-curable polymer dispersed in water, wherein the method comprises removing the base coat to effect removal of the base coasts as well as the color coat.

In another embodiment the invention comprises a kit for a nail composition system, said kit comprising:

(1) at least one base coat composition comprising a polymer dispersed in water (latex); and (2) at least one color coat composition comprising a photo-curable polymer dispersed in water (latex).

Optionally, the kit further comprises a topcoat composition optionally comprising a polymer dispersed in water (latex).

In another embodiment the invention comprises a method of making a cosmetic composition for application to the nails comprising:

(1) combining:
  (a) from about 6% to about 20%, by dry weight, of at least one photo-curable polymer dispersed in water;
  (b) from about 6% to about 20%, by dry weight, of at least one non-photo-curable polymer dispersed in water;
  (c) less than or equal to about 2% by weight of at least one photo-initiator;
  (d) from about 0% to about 8% by weight of at least one plasticizer;
  (e) optionally a colorant; and
  (f) from about 40% to about 70% water;
  wherein the ratio, by dry polymer weight, of the at least one photo-curable polymer (a) to the at least one non-photo-curable polymer (b) is from about 4:1 to about 1:5, and the sum, by dry polymer weight percent, of the photo-curable polymer (a) plus the non-photo-curable polymer (b) is from about 25% to about 40%; all weights being relative the total weight of the composition; and (2) mixing the foregoing components.

Polymers Dispersed in Water—Latexes

As indicated above, the composition of the invention comprises at least one photo-curable and at least one non-photo-curable polymer dispersed in water. A polymer dispersed in water is commonly referred to as a "latex".

Generally, a "latex" is a colloidal dispersion of polymer particles in an aqueous liquid phase. Such latexes can be obtained by polymerization or copolymerization of monomers that are usually emulsified in an aqueous medium according to processes that are well known to those of ordinary skill in the art. See, e.g., U.S. Pat. No. 5,731,134. Alternatively, latexes can be formed by dispersing a finely divided, preformed water-insoluble polymer in water. See, e.g., U.S. Pat. No. 8,088,414.

The monomers which are polymerized to result in the latex dispersion may be chosen in particular from styrene, butadiene, acrylonitrile, chloroprene, vinyl acetate, urethanes, isoprene, isobutylene, and acrylic or methacrylic acid, maleic acid, crotonic acid or itaconic acid or esters or amides thereof. Latexes are sometimes referred to as water-dispersions, such as "water-dispersed polymers".

As mentioned above, the total amount of the polymer in the dispersion is known as the "solids content" of the latex. The remainder of the latex is primarily water. Depending on the source, the latex may include small amounts of preservatives and such other additives that to not interfere with the latex's ability to form a film.

"Water-dispersible" with respect to the film forming polymer herein means that the polymer is dispersible in water at 25° C. in an amount of at least 30%, optionally in the presence of a surfactant.

In the instant composition, the combined amount of latexes (that is photo-curable latexes+non-photo-curable latexes) by dry weight is from about 25% to about 40%, by dry weight, typically from about 27% to about 37%, more typically from about 29% to about 35%.

Photo-curable Latexes (a)

The polymers in the photo-curable latexes of the invention have high molecular weights (number average molecular weight ("Mn") greater than about 9,000 Daltons, preferably greater than 10,000 Daltons), are pre-polymerized and have functional groups that are reactive by exposure to active energy radiation. By "pre-polymerized" it is meant that the polymers of the invention are fully polymerized prior to use in the compositions of invention. By "reactive" it is meant the polymers have functional groups that cross-link, thereby forming a 3-D network, when exposed to energy radiation such as UV light in the presence of a photo-initiator, but do not further polymerize. Such polymers are described, for example, in US Pat. App. No 2010/0160475 (BASF) and WO2014/033656, both herein incorporated by reference. As these are latexes, the polymer is water-dispersed (waterborne) and the resulting dispersion is stable.

As stated above, the latexes of the invention are stable colloidal dispersions of polymers in water. As such, these latexes are distinguishable from compositions containing monomers and/or oligomers which have an Mn less than about 8000 Da and which are still polymerizable.

The at least one photo-curable latex has film-forming properties that advantageously imparts adhesive properties to the inventive composition. That is, the latex aids in adhering the composition to the nail. The photo-curable latex (and necessarily the photo-curable polymer therein) is thus a film-former as that term in herein defined.

Non-limiting examples of specific types of film-forming photo-curable latexes are provided below.

Aliphatic and/or Aromatic Acrylated Urethane Dispersions

As used herein, acrylated polyurethane polymer is synonymous with a polyurethane acrylate polymer.

Representative examples of suitable pre-polymerized, photo-curable latexes include the aqueous dispersions of polyfunctional (meth)acrylate polyurethanes commercially available from DSM under the names NeoRad™, such as, for example, NeoRad™ R465 (aliphatic urethane acrylic copolymer), NeoRad™ R452 (aliphatic urethane acrylic copolymer), and mixtures thereof.

Other examples of suitable pre-polymerized aromatic polyurethanes include those commercially available from BASF under the name Laromer LR™ such as Laromer LR™ 8983 and Laromer LR 8949, as well as those sold by Bayer under the name Bayhydrol™ UV, such as Bayhydrol™ UV XP 2689, Bayhydrol™ UV XP 2775, Bayhydrol UV XP 2649 (anionic) and Bayhydrol™ UV2280, and mixtures of all of these.

In an embodiment, the polymer in the photo-curable latexes has a number average molecular weight (Mn) greater than about 10,000, typically from about 10,100 to about 500,000, more typically from about 16,000 to about 50,000

In an embodiment, the polymer in the photo-curable latexes has a Tg prior to curing of from about −8° C. to about 70° C., including from about 0° C. to about 60° C., more typically from about 20° C. to about 55° C., most typically about 50° C.

In an embodiment the photo-curable latexes have a solids contents of from about 10% to about 18%, and a water contents of from about 50% to about 70%.

Non-limiting examples of suitable photo-curable latexes are provided in Table 1 below. Mixtures of the below latexes may also be used.

TABLE 1 photo-curable (UV) latexes

| Name | Supplier | Mn Determined bySEC* | Tg (° C.) (of dry latex measured by DSC)** |
|---|---|---|---|
| NeoRad ® R-441 (Nonionic, acrylic functional aliphatic urethane) | DSM | | |
| NeoRad ® R-449 (Aliphatic, urethane/acrylic copolymer) | DSM | | |
| NeoRad ® R-465 (Aliphatic, urethane/acrylic copolymer) | DSM | 16700 | 51 |
| NeoRad ® R-452 (Aliphatic, urethane/acrylic copolymer) | DSM | 421400 | 13 |
| NeoRad ® R-440 (Anionic, aliphatic urethane dispersion) | DMS | | |
| urethane acrylate emulsion | BASF | | |
| polyester acrylate | BASF | | |
| aromatic polyurethane dispersion | BASF | | |
| Bayhydrol ® UV XP 2775 (urethane acrylate dispersion) | Bayer | 11200 | 23 |
| urethane acrylate emulsion | Bayer | | |
| aliphatic anionic polyurethane dispersion | Bayer | | |
| Bayhydrol ® UV 2280 (urethane acrylate dispersion) | Bayer | | 57 |
| Ucecoat ® 7733 (aliphatic acrylated polyurethane dispersion) | Allnex | 13600 | 0 |
| Ucecoat ® 7773 (acrylated polyurethane dispersion) | Allnex | 12300 | −7 |
| Ucecoat ® 7849 (acrylated polyurethane dispersion) | Allnex | 13700 | 30 |

*SEC in the above table means size exclusion chromatography.
**DSC in the above table means differential scanning calorimetry.

Particularly suitable photo-curable latexes include the aqueous dispersions of polyurethane available under the following brand names and suppliers: NeoRad™ R465 and NeoRad™ R452 (DSM, aliphatic, urethane/acrylic copolymer); Ucecoat 7773 and Ucecoat 7849 (from Allnex, acrylated polyurethane dispersion); and mixtures thereof.

Typically, the photo-curable polymer is present in the compositions of the invention (as measured in amounts of polymer solids content in the latex dispersion) generally ranging from about 6% to about 20%, typically from about 10% to about 18%, more typically from about 14% to about 17%, by dry weight, based on the total weight of the composition, including all ranges and subranges in between.

Latexes are water-based, meaning that the continuous phase is water. Preferably, total water content present in the photo-curable latex is in amounts generally ranging from about 45% to about 75%, more preferably from about 50% to about 70%, and more preferably from about 52% to about 65%, by weight, based on the total weight of the composition, including all ranges and subranges in between.

The Non-Photo-Curable Latex (b)

As indicated above, the composition of the invention comprises at least one non-photo-curable polymer dispersed in water (non-photo-curable latex). Non-photo-curable polymers do not have reactive pendant (meth)acrylate functional groups. These polymers are thus not "curable" as they lack the exposed functional groups that typically react when treated with radiant energy.

In an embodiment, the at least one non-photo-curable polymer has at least one Tg at or below room temperature (about 25° C.). In this embodiment, the plasticizer may be omitted.

Specific examples of types of non-photo-curable acrylate polymers as well as specific examples of such polymers include:

- synthetic polymers of the polycondensate type or of the free-radical type;
- acrylic polymers resulting from the copolymerization of monomers chosen from the esters and/or amides of acrylic acid or of methacrylic acid. As examples of monomers of ester type, mention may be made of methyl methacrylate, ethyl methacrylate, butyl methacrylate, isobutyl methacrylate, 2-ethylhexyl methacrylate and lauryl methacrylate. As examples of monomers of amide type, mention may be made of N-t-butylacrylamide and N-t-octylacrylamide;
- acrylic polymers obtained by copolymerization of ethylenically unsaturated monomers containing hydrophilic groups, preferably of nonionic nature, such as hydroxyethyl acrylate, 2-hydroxypropyl acrylate, hydroxyethyl methacrylate and 2-hydroxypropyl methacrylate;
- vinyl polymers resulting from the homopolymerization or copolymerization of monomers chosen from vinyl esters, styrene or butadiene. As examples of vinyl esters, mention may be made of vinyl acetate, vinyl neodecanoate, vinyl pivalate, vinyl benzoate and vinyl t-butylbenzoate;
- acrylic/silicone copolymers;
- polymers resulting from the free-radical polymerization of one or more free-radical monomers inside and/or partially at the surface of preexisting particles of at least one polymer chosen from the group consisting of polyurethanes, polyureas, polyesters, polyesteramides and/or alkyds. These polymers are generally referred to as "hybrid polymers";
- and bimodal film forming agents which form a bimodal interpenetrating network containing multiple functionalities (for example, cationic and anionic functionalities) which is reversibly cross-linked at least partially through the multiple functionalities are disclosed in PCT patent application nos. WO 05/087191 and WO 06/028931, and corresponding U.S. provisional application Nos. 60/551,658, 60/606,985, and 60/627,224, the entire contents of all of which are hereby incorporated by reference in their entirety. Suitable bimodal film forming agents include, but are not limited to, film forming agents having both cationic and anionic functionalities. According to particularly preferred embodiments of the present invention, the bimodal film forming agent comprises at least one acrylic acid-based, (meth)acrylic acid-based, acrylate-based or (meth)acrylate-based monomer having anionic and/or cationic functionalities. Suitable polymers or copolymers include, but are not limited to, polymers comprising polyacrylates such as those identified in the International Cosmetic Ingredient Dictionary and Handbook (9.sup.th ed. 2002) such as, for example, polyacrylate-1, polyacrylate-2, polyacrylate-3, polyacrylate-4, polyacrylate-16, polyacrylate-17, polyacrylate-18, polyacrylate-19, etc. Such (co)polymers, or similar (co)polymers, can be combined individually or with other (co)polymers in such a way to form suitable bimodal film forming agents having both cationic and anionic functionalities. According to particularly preferred embodiments, the bimodal film forming agent is selected from the group consisting of polymers consisting of polyacrylate-21 and acrylates/dimethylaminoethylmethacrylate copolymer (marketed under the name Syntran PC 5100 by Interpolymer), polyacrylate-16 (marketed under the name Syntran PC 5112 by Interpolymer), polyacrylate-18 and polyacrylate-19 (marketed under the name Syntran PC 5107 by Interpolymer), and polyacrylate-18 and polyacrylate-1 g (marketed under the name Syntran PC 5117 by Interpolymer). The bimodal film forming agent containing polyacrylate-21 and acrylates/dimethylaminoethylmethacrylate copolymer (Syntran PC 5100) and polyacrylate-16 (Syntran PC 5112) are particularly preferred.

Representative examples of suitable non-photo-curable polymers dispersed in water (latexes) include acrylic copolymer dispersions sold under the names Neocryl® XK-90 (acrylic/styrene copolymer), Neocryl A-1070® (acrylic/styrene copolymer), Neocryl A-1090® (acrylic/styrene copolymer), Neocryl BT-62® (acrylic/styrene copolymer), Neocryl A-1079® (acrylic/styrene copolymer) and Neocryl A-523® (acrylic/styrene copolymer) by the company Avecia-Neoresins; NeoCryl® XK-320 (acrylic/styrene copolymer emulsion), and NeoCryl® A-1120 (acrylic/styrene copolymer dispersion) by the company DSM; Dow Latex 432® (styrene/acrylates copolymer) by the company Dow Chemical; Syntran® PC 5620 (styrene/acrylates copolymer) by the company Interpolymer; Daitosol 5000 AD® (acrylates copolymer) by the company Daito Kasey Kogyo; or the aqueous dispersions of polyurethane sold under the names Neorez R-981® (INCI name: polyester-polyurethane copolymer) and Neorez R-974® (INCI name: polyester-polyurethane copolymer) by the company Avecia-Neoresins, Avalure UR-405® (INCI name: polyurethane-2), Avalure UR-410® (INCI name: polyurethane-2), Avalure UR-425° (INCI name: polyurethane-2), Avalure UR-450® NCI name: PPG-17/IPDI/DMPA copolymer), Sancure 875® (INCI name: polyester-polyurethane copolymer), Sancure 861® (INCI name: polyester-polyurethane copolymer), Sancure 878® (INCI name: polyester-polyurethane copolymer) and Sancure 2060° (INCI name: polyester-polyurethane copolymer) by the company Goodrich, Impranil 85® (INCI name: Water and Polyurethane/Polyester) by the company Bayer and Aquamere H-1511® (INCI name: PVP/polycarbamyl/polyglycol Ester) by the company Hydromer.

Further examples of non-photo curable polymers and latexes useful in the present invention include (meth)acrylate copolymers such as, for example, acrylate copolymers (acrylates/ethylhexyl acrylate copolymer, sold by Daito Kasei under the tradename Daitosol 5000SJ), butyl acrylate/hydroxypropyl dimethicone acrylate copolymers (Granacrysil BAS by Grant Industries, Inc.), acrylates/C12-C22 alkylmethacrylate copolymers (Allianz OPT by ISP), isododecane and acrylates copolymers (Giovarez AC-5099M by Phoenix), and acrylates/octylacrylamide copolymers (Dermacryl-79 by National Starch & Chemical Company).

Still further examples of suitable non-photo-curable polymers (polyurethanes) and latexes include those disclosed in U.S. Pat. Nos. 7,445,770 and/or 8,114,938, the entire contents of both of which are hereby incorporated by reference. For example, suitable latexes include aqueous polyurethane dispersions including the reaction products of:
A) a pre-polymer according to the formula:

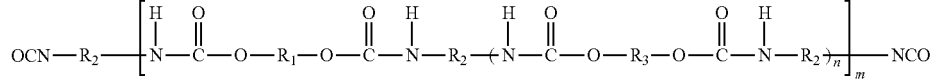

wherein $R_1$ represents a bivalent radical of a dihydroxyl functional compound, $R_2$ represents a hydrocarbon radical of an aliphatic or cycloaliphatic polyisocyanate, $R_3$ represents a radical of a low molecular weight diol, optionally substituted with ionic groups, n is from 0 to 5, and m is >1;
B) at least one chain extender according to the formula: $H_2N-R_4-NH_2$ wherein $R_4$ represents an alkylene or alkylene oxide radical not substituted with ionic or potentially ionic groups; and
C) at least one chain extender according to the formula: $H_2N-R_5-NH_2$ wherein $R_5$ represents an alkylene radical substituted with ionic or potentially ionic groups.

Suitable dihydroxyl compounds for providing the bivalent radical $R_1$ include those having two hydroxy groups and having number average molecular weights of from about 700 to about 16,000, and preferably from about 750 to about 5000. Examples of the high molecular weight compounds include polyester polyols, polyether polyols, polyhydroxy polycarbonates, polyhydroxy polyacetals, polyhydroxy polyacrylates, polyhydroxy polyester amides, polyhydroxy polyalkadienes and polyhydroxy polythioethers. The polyester polyols, polyether polyols and polyhydroxy polycarbonates are preferred. Mixtures of various such compounds are also within the scope of the present invention.

Suitable polyisocyanates for providing the hydrocarbon radical $R_2$ include organic diisocyanates having a molecular weight of from about 112 to 1,000, and preferably from about 140 to 400. Preferred diisocyanates are those represented by the general formula $R_2(NCO)_2$ indicated above in which $R_2$ represents a divalent aliphatic hydrocarbon group having from 4 to 18 carbon atoms, a divalent cycloaliphatic hydrocarbon group having from 5 to 15 carbon atoms, a divalent araliphatic hydrocarbon group having from 7 to 15 carbon atoms or a divalent aromatic hydrocarbon group having 6-15 carbon atoms. Examples of the organic diisocyanates which are suitable include tetramethylene diisocyanate, 1,6-hexamethylene diisocyanate, dodecamethylene diisocyanate, cyclohexane-1,3- and -1,4-diisocyanate, 1-isocyanato-3-isocyanatomethyl-3,5,5-trimethylcyclohexane (isophorone diisocyanate or IPDI), bis-(4-isocyanatocyclohexyl)-methane, 1,3- and 1,4-bis(isocyanatomethyl)-cyclohexane, bis-(4-isocyanato-3-methyl-cyclohexyl)-methane, isomers of toluene diisocyanate (TDI) such as 2,4-diisocyanatotoluene, 2,6-diisocyanatotoluene, mixtures of these isomers, hydrogenated TDI, 4,4'-diisocyanato diphenyl methane and its isomeric mixtures with 2,4'- and optionally 2,2'-diisocyanato diphenylmethane, and 1,5-diisocyanato naphthalene. Mixtures of diisocyanates can, of course, be used. Preferred diisocyanates are aliphatic and cycloaliphatic diisocyanates. Particularly preferred are 1,6-hexamethylene diisocyanate and isophorone diisocyanate.

"Low molecular weight diols" in the context of $R_3$ means diols having a molecular weight from about 62 to 700, preferably 62 to 200. They may contain aliphatic, alicyclic or aromatic groups. Preferred compounds contain only aliphatic groups. The low molecular weight diols having up to about 20 carbon atoms per molecule include ethylene glycol, diethylene glycol, propane 1,2-diol, propane 1,3-diol, butane 1,4-diol, butylene 1,3-glycol, neopentyl glycol, butyl ethyl propane diol, cyclohexane diol, 1,4-cyclohexane dimethanol, hexane 1,6-diol, bisphenol A (2,2-bis(4-hydroxyphenyl) propane), hydrogenated bisphenol A (2,2-bis(4-hydroxycyclohexyl)propane), and mixtures thereof. Optionally, the low molecular weight diols may contain ionic or potentially ionic groups. Suitable lower molecular weight diols containing ionic or potentially ionic groups are those disclosed in U.S. Pat. No. 3,412,054, the contents of which is hereby incorporated by reference. Preferred compounds include dimethylol butanoic acid (DMBA), dimethylol propionic acid (DMBA) and carboxyl-containing caprolactone polyester diol. If lower molecular weight diols containing ionic or potentially ionic groups are used, they are preferably used in an amount such that <0.30 meq of COOH per gram of polyurethane in the polyurethane dispersion are present.

The prepolymer is chain extended using two classes of chain extenders. First, compounds having the formula: $H_2N-R_4-NH_2$ wherein $R_4$ represents an alkylene or alkylene oxide radical not substituted with ionic or potentially ionic groups. Alkylene diamines include hydrazine, ethylenediamine, propylenediamine, 1,4-butylenediamine and piperazine. The alkylene oxide diamines include 3-{2-[2-(3-aminopropoxy)ethoxy]ethoxy}propylamine (also known as dipropylamine diethyleneglycol or DPA-DEG available from Tomah Products, Milton, Wis.), 2-methyl-1,5-pentanediamine (Dytec A from DuPont), hexane diamine, isophorone diamine, and 4,4-methylenedi-(cyclohexylamine), and the DPA-series ether amines available from Tomah Products, Milton, Wis., including dipropylamine propyleneglycol, dipropylamine dipropyleneglycol, dipropylamine tripropyleneglycol, dipropylamine poly(propylene glycol), dipropylamine ethyleneglycol, dipropylamine poly(ethylene glycol), dipropylamine 1,3-propane diol, dipropylamine 2-methyl-1,3-propane diol, dipropylamine 1,4-butane diol, dipropylamine 1,3-butane diol, dipropylamine 1,6-hexane diol and dipropylamine cyclohexane-1,4-dimethanol. Mixtures of the listed diamines may also be used.

The second class of chain extenders are compounds having the formula: $H_2N-R_5-NH_2$ wherein $R_5$ represents an alkylene radical substituted with ionic or potentially ionic groups. Such compounds have an ionic or potentially ionic group and two groups that are reactive with isocyanate groups. Such compounds contain two isocyanate-reactive groups and an ionic group or group capable of forming an ionic group. The ionic group or potentially ionic group can be selected from the group consisting of ternary or quaternary ammonium groups, groups convertible into such a group, a carboxyl group, a carboxylate group, a sulfonic acid group and a sulfonate group. The at least partial conversion of the groups convertible into salt groups of the type mentioned may take place before or during the mixing with water. Specific compounds include diaminosulfonates, such as for example the sodium salt of N-(2-aminoethyl)-2-aminoethane sulfonic acid (AAS) or the sodium salt of N-(2-aminoethyl)-2-aminopropionic acid.

Commercially available examples of such latexes include, but are not limited to, aqueous polyurethane dispersions comprising a reaction product of a prepolymer comprising a dihydroxyl compound, a polyisocyanate, and a low molecular weight diol and at least two diamine compounds and wherein the composition is substantially free of triethanolamine stearate such as, for example, those sold under the BAYCUSAN® name by Bayer such as, for example, BAYCUSAN® C1000 (polyurethane-34), BAYCUSAN® C1001 (polyurethane-34), BAYCUSAN® C1003 (polyurethane-32), and BAYCUSAN® C1004 (polyurethane 35).

Finally, suitable examples of non-photo-curable polymers and latexes can be found, for example, in U.S. patent application Ser. Nos. 61/541,173, 61/542,131, and 61/542,136, U.S. patent application publication no. 2008/0081054, and U.S. Pat. Nos. 5,538,717, 5,672,647, 6,297,950 and 6,372,201, the entire contents of all of which are hereby incorporated by reference.

Particularly suitable non-photo-curable latexes are provided below in Table 2. Mixtures of the below latexes may also be used.

TABLE 2

Non-photo-curable latexes

| Name | Supplier | Tg (° C.) (dried latex) |
| --- | --- | --- |
| Baycusan ™ C1004 (INCI: polyurethane-35 dispersion) | Bayer | −47 |
| NeoCryl ™ A-1120 (acrylic/styrene copolymer dispersion) | DSM | −44 |
| NeoCryl ™ XK-320 (acrylic/styrene copolymer emulsion) | DSM | −0.5 and 60.3 (has two Tgs) |
| Syntran ™ PC5620 (INCI: styrene/acrylates/ammonium methacrylate) copolymer | Interpolymer | 44 |

Typically, the non-photo-curable polymer is present in the compositions of the invention (as measured in amounts of polymer solids content in the latex dispersion) in amounts equal to or greater than about 10%, such as from about 10% to about 30%, typically from about 12% to about 25%, more typically from about 14% to about 20%, by dry weight, based on the total weight of the composition, including all ranges and subranges therebetween.

In the instant compositions, the ratio by dry weight of the at least on photo-curable latex (a) to the at least one non-photo-curable latex (b) is from about 4:1 to about 1:5, typically from about 3:2 to about 1:3, more typically from about 1:1.03 to about 1:1.11.

In an embodiment the at least one water-dispersed non-photo-curable polymer has at least one Tg equal to or less than about 25° C. (dry latex). In a particular embodiment, the at least one water-dispersed non-photo-curable polymer has a Tg of the dried latex lower than about 0° C., including specifically lower than −44° C. When the non-photo-curable polymer has a Tg lower than about room temperature (about 25° C.), a plasticizer is not needed in the inventive composition.

Photo-initiator (c)

As described herein, the cosmetic composition comprises at least one photo-initiator having an absorption wavelength greater than about 200 nm.

The at least one photo-initiator may exhibit at least one absorption peak at a wavelength greater than about 200 nm, such as greater than about 260 nm up to about 400 nm. The at least one photo-initiator may be active at visible light wavelengths, e.g., wavelengths greater than about 400 nm, for instance, wavelengths ranging from about 400 nm to about 500 nm.

According to various embodiments of the disclosure, the at least one photo-initiator having at least one absorption wavelength greater than about 200 nm may be chosen from monoacylphosphine oxides and bisacylphosphine oxides, red-shifted phenylglyoxylates, red-shifted benzophenones, and isoproylthioxanthones having at least one absorption wavelength greater than about 200 nm. Exemplary mono- and bisacylphosophine oxide photo-initiators suitable for use in accordance with the present invention are disclosed, for example, in U.S. Pat. Nos. 4,324,744, 4,737,593, 5,942,290, 5,534,559, 6,020,528, 6,486,226, and 6,486,228, the disclosures of which are incorporated herein by reference in their entireties.

By way of non-limiting example only, suitable monoacylphosphine oxides may be chosen from compounds of general formula (III):

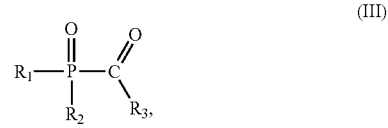

wherein:
  $R_1$ is chosen from $C_1$-$C_{12}$ alkyl, benzyl, and phenyl radicals optionally substituted with at least one substituent chosen from halogens and $C_1$-$C_8$ alkyl and alkoxy radicals; cyclohexyl radicals; and —$OR_4$ radicals, wherein $R_4$ is chosen from $C_1$-$C_8$ alkyl, phenyl, and benzyl radicals;
  $R_2$ is chosen from $C_1$-$C_{12}$ alkyl, benzyl, and phenyl radicals optionally substituted with at least one substituent chosen from halogens and $C_1$-$C_8$ alkyl and alkoxy radicals; and cyclohexyl radicals; and $R_3$ is chosen from phenyl radicals optionally substituted with at least one substituent chosen from halogens and $C_1$-$C_8$ alkyl, alkoxy, and alkylthio radicals.

For example, in at least one embodiment, $R_1$ may be chosen from —$OR_4$ and phenyl radicals, $R_2$ may be chosen from phenyl radicals optionally substituted with at least one substituent chosen from halogens and $C_1$-$C_8$ alkyl and alkoxy radicals, and $R_3$ may be chosen from phenyl groups optionally substituted with at least one $C_1$-$C_8$ alkyl radical. In another embodiment, $R_1$ and $R_2$ are phenyl groups. According to at least one exemplary embodiment, the monoacylphosphine oxide is chosen from 2,4,6-trimethylbenzoylethoxyphenylphosphine oxide and 2,4,6-trimethylbenzoyldiphenylphosphine oxide.

Non-limiting examples of suitable bisacylphosphine oxides include those of general formula

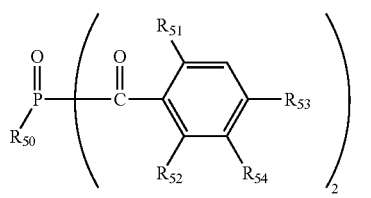

(IV)

wherein:

$R_{50}$ is chosen from $C_1$-$C_{12}$ alkyl, cyclohexyl, and phenyl radicals optionally substituted with at least one substituent chosen from halogens and $C_1$-$C_8$ alkyl radicals, $SR_{10}$, and $N(R_{11})(R_{12})$, wherein:

$R_{10}$, $R_{11}$, and $R_{12}$ are independently chose from hydrogen, $C_1$-$C_{24}$ alkyl radicals, $C_2$-$C_{24}$ alkenyl radicals, $C_3$-$C_8$ cycloalkyl radicals, phenyl radicals, benzyl radicals, and $C_2$-$C_{20}$ alkyl radicals interrupted by at least one non-consecutive oxygen atom and optionally substituted by at least one group chosen from —OH and —SH, or $R_{11}$ and $R_{12}$, together with the nitrogen atom to which they are bonded, form a 5- or 6-membered ring, optionally comprising at least one entity chosen from oxygen, sulfur, and $NR_{13}$, wherein $R_{13}$ is chosen from hydrogen, phenyl radicals, $C_1$-$C_{12}$ alkoxy radicals, $C_1$-$C_{12}$ alkyl radicals, and $C_2$-$C_{12}$ alkyl radicals interrupted by at least one non-consecutive oxygen atom and optionally substituted by at least one group chosen from —OH and —SH;

$R_{51}$ and $R_{52}$ are independently chosen from $C_1$-$C_8$ alkyl and alkoxy radicals;

$R_{53}$ is chosen from hydrogen and $C_1$-$C_{10}$ alkyl radicals; and $R_{54}$ is chosen from hydrogen and methyl radicals.

According to various exemplary embodiments, the at least one photo-initiator having at least one absorption wavelength greater than about 200 nm may be chosen from bisacylphosphine oxides of formula (IV), wherein $R_{50}$ is chosen from $C_2$-$C_{10}$ alkyl, cyclohexyl, and phenyl radicals optionally substituted with at least one substituent chosen from $C_1$-$C_4$ alkyl radicals, chlorine, and bromine. In one non-limiting embodiment, $R_{50}$ is chosen from $C_3$-$C_8$ alkyl, cyclohexyl, and phenyl radicals optionally substituted on the 2-, 3-, 4-, or 2,5-positions by a $C_1$-$C_4$ alkyl radical. For example, $R_{50}$ may be chosen from $C_4$-$C_{12}$ alkyl and cyclohexyl radicals, $R_{51}$ and $R_{52}$ may be independently chosen from $C_1$-$C_8$ alkoxy radicals, and $R_{53}$ may be chosen from hydrogen and $C_1$-$C_4$ alkyl groups. In at least one further exemplary embodiment, $R_{51}$ and $R_{52}$ may be independently chosen from methyl and methoxy radicals, and $R_{53}$ may be chosen from hydrogen and methyl radicals. According to yet another exemplary embodiment, the radicals $R_{51}$, $R_{52}$, and $R_{53}$ are methyl radicals. In a further exemplary embodiment, the radicals $R_{51}$, $R_{52}$, and $R_{53}$ are methyl radicals and $R_{54}$ is hydrogen.

For example, $R_{50}$ may be chosen from $C_3$-$C_8$ alkyl radicals. In one exemplary embodiment, $R_{50}$ may be chosen from isobutyl and phenyl radicals. In another exemplary embodiment, $R_{51}$ and $R_{52}$ are methoxy radicals, $R_{53}$ and $R_{54}$ are hydrogen, and $R_{50}$ is an isooctyl radical. According to at least one exemplary embodiment, the bisacylphosphine oxide is chosen from bis(2,4,6-trimethylbenzoyl)-phenylphosphine oxide, bis(2,4,6-trimethylbenzoyl)-(2,4-bis-pentyloxyphenyl) phosphine oxide, and bis(2,6-dimethoxybenzoyl)-2,4,4-trimethylpentylphosphine oxide.

According to various exemplary embodiments, the at least one photo-initiator having at least one absorption wavelength greater than about 200 nm is chosen from bis(2,4,6-trimethylbenzyol)-phenyl phosphine oxide and ethyl-2,4,6-trimethylbenzoylphenylphosphinate. Exemplary such commercial photo-initiator products are available from BASF Resins under the names IRGACURE® 2100, IRGACURE® 819, and LUCIRIN® TPO-L; the product sold by Cytec Industries, Inc. under the name ADDITOL® TPO; and the product sold by Lamberti under the name ESACURE® TPO, and mixtures thereof.

The total amount of the at least one photo-initiator having at least one wavelength greater than about 200 nm (c) is less than or equal to about 2%, typically from about 0.5% to about 1.9%, more typically from about 1% to about 1.8%, more particularly about 1.7%, by weight, including all ranges and subranges therebetween, all weights being based on the total weight of the composition.

The Plasticizer (d)

The composition of the invention optionally may include a plasticizer.

Plasticizers are additives used to optimize the mechanical properties of the films. They tend to reduce the Glass Transition Temperature (Tg) and increase the softness and flexibility of the films.

When present in the inventive compositions, the plasticizer preferably has a distribution coefficient D of less than or equal to 0.1. The distribution coefficient can be determined in accordance with the teaching of "A method to predict the distribution coefficient of coalescing agents between latex particles and the water phase," *Progress in Organic Coatings*, vol. 30, 1997, pp. 173-177, the disclosure of which is specifically incorporated by reference herein.

Preferably, the plasticizer has a boiling point measured at ambient pressure of less than or equal to 285° C., preferably less than or equal to 270° C., and preferably less than or equal to 250° C. In the present specification, the boiling point values are to be considered accurate to ±2° C. owing to the uncertainties of boiling point measurement.

Any plasticizing agent typically found in nail polish compositions can be used. Examples of suitable plasticizers include, but are not limited to, glycols and their ester derivatives, esters of acids, in particular carboxylic acids, such as citrates, adipates, carbonates, tartrates, phosphates or sebacates, oxyethylenated derivatives, such as oxyethylenated oils, and their mixtures. For example, suitable plasticizing agents include, but are not limited to, diisobutyl adipate, the ester of teributyl acid and 2,2,4-trimethylpentane-1,3-diol, diethyl adipate, diethyl phthalate, dibutyl phthalate, dioctyl phthalate, butyl 2-ethylhexyl phthalate, dimethyl sebacate, dibutyl sebacate, ethyl stearate, 2-ethylhexyl palmitate, dipropylene glycol n-butyl ether, dipropylene glycol dibenzoate, tributyl phosphate, tributoxyethyl phosphate, tricresyl phosphate, triphenyl phosphate, glycerol triacetate, butyl stearate, butyl glycolate, benzyl benzoate, butyl acetyltricinoleate, glyceryl acetyltricinoleate, dibutyl phthalate, diisobutyl phthalate, dioctyl phthalate, dimethoxyethyl phthalate, diamyl phthalate, triethyl citrate, tributyl citrate, tributyl acetylcitrate, tri(2-ethylhexyl) acetylcitrate, dibutyl tartrate, camphor, trimethylhydroxypenta isobuterate, and mixtures thereof.

In an embodiment the plasticizer is selected from dipropylene glycol dibenzoate, tributyl citrate, and mixtures thereof.

The plasticizer is present in an amount of from about 0% to about 8% by weight, typically from about 0.5% to about 3% by weight, most typically from about 1% to about 2.5% by weight, particularly about 2% by weight, relative to the weight of the composition, including all ranges and subranges therebetween.

The Colorant (Optional) (e)

The compositions of the invention preferably are used as a color coat for application to nails. When used as a color coat, the composition comprises at least one colorant. Any colorant typically found in nail polish compositions can be used. Suitable colorants include, but are not limited to, lipophilic dyes, pigments and pearlescent agents, and their mixtures.

Suitable examples of fat-soluble dyes are, for example, Sudan red, DC Red 17, DC Green 6, β-carotene, soybean oil, Sudan brown, DC Yellow 11, DC Violet 2, DC Orange 5 and quinoline yellow.

Suitable pigments can be white or colored, inorganic and/or organic and coated or uncoated. Mention may be made, for example, of inorganic pigments such as titanium dioxide, optionally surface treated, zirconium or cerium oxides and iron or chromium oxides, manganese violet, ultramarine blue, chromium hydrate and ferric blue. Mention may also be made, among organic pigments, of carbon black, pigments of D & C type and lakes based on cochineal carmine or on barium, strontium, calcium or aluminum, such as D&C Red No. 10, 11, 12, and 13, D&C Red No. 7, D&C Red No. 5 and 6, and D&D Red No. 34, as well as lakes such as D&C Yellow Lake No. 5 and D&C Red Lake No. 2.

Suitable pearlescent pigments can be chosen from, for example, white pearlescent pigments, such as mica covered with titanium oxide or with bismuth oxychloride, colored pearlescent pigments, such as titanium oxide-coated mica with iron oxides, titanium oxide-coated mica with in particular ferric blue or chromium oxide, or titanium oxide-coated mica with an organic pigment of the abovementioned type, and pearlescent pigments based on bismuth oxychloride.

In accordance with preferred embodiments, the colorant is preferably present in the color coat in an amount of from about 0.01% to about 10% by weight, typically from about 0.5% to 5% by weight, particularly from about 0.75% to about 4.5% by weight, of the total weight of the composition, including all ranges and subranges therebetween.

Water (f)

The compositions of the invention, in particular the color coats, include water. The water is present in an amount of from about 40% to about 70%, typically from about 50% to about 68%, more typically from about 52% to about 65%, by weight relative to the weight of the composition, including all ranges and subranges therebetween.

Coalescents (Optional)

Coalescents may be present in any or all of the coats of a nail system (base, color and/or top coats). When a base coat is used, it preferably comprises at least one coalescent agent. Coalescents are additives used to aid the coalescence of the latex particles, and hence assisting the film formation process. The coalescent agent promotes the coalescence of the polymer(s) in the composition.

Preferably, the coalescent agent has a distribution coefficient D' of greater than or equal to 0.5, measured in accordance with the above-referenced "A method to predict the distribution coefficient of coalescing agents between latex particles and the water phase," *Progress in Organic Coatings*, vol. 30, 1997, pp. 173-177.

Preferably, the coalescent agent has a boiling point measured at ambient pressure ranging from 90° C. to 180° C., preferably from 150° C. to 180° C.

Any coalescent agent typically found in nail polish compositions can be used. A non-limiting example of a coalescent is propylene glycol.

If present, the coalescent agent is preferably present in the base, color or top coat in an amount of from 0.05% to 8% by weight, preferably from 0.1% to 4% by weight, preferably from 0.2 to 1% by weight relative of the weight of the composition, including all ranges and subranges therebetween.

Auxiliaries/Additives (Optional)

The nail compositions of the present invention may comprise additional additive or auxiliary components commonly used in cosmetic compositions and known to a person skilled in the art as being capable of being incorporated into a nail polish or varnish composition. Such additives or auxiliaries may be chosen from thickeners, additional coalescents, preservatives (e.g. caprylyl glycol), fragrances, oils, waxes, surfactants, antioxidants, agents for combating free radicals, spreading agents, wetting agents, dispersing agents, antifoaming agents, neutralizing agents, stabilizing agents, active principles chosen from essential oils, UV screening agents, sunscreens, moisturizing agents, vitamins, proteins, ceramides, plant extracts, fibers, and the like, and their mixtures.

A person skilled in the art will take care to select the optional additional additives and/or the amount thereof such that the advantageous properties of the composition according to the invention are not, or are not substantially, adversely affected by the envisaged addition. These substances may be selected variously by the person skilled in the art in order to prepare a composition which has the desired properties, for example, consistency or texture.

These additives may be present in the composition in a proportion from 0% to 10% by weight, typically from about 0.5% to about 8%, by weight, more typically from about 1% to about 5% by weight, particularly from about 1.2% to about 3%, by weight relative to the weight of the composition, including all ranges and subranges therebetween.

Nail Composition System

In an embodiment, the present invention provides a nail coloring system comprising at least one base coat and at least one color coat. The color coat is a composition according to the invention as described above. The nail system of the present invention can optionally further comprise a top coat.

It should be understood that each coat or layer in the nail composition system, itself, can comprise one or more layers of each composition. Thus, the at least one base coat can comprise one or more base coat layers; the at least one color coat can comprise one or more color coat layers; and the at least one top coat can comprise one or more top coat layers. Preferably, each base coat, color coat and top coat contains three or fewer layers of composition, more preferably two or fewer layers of composition, and most preferably a single layer of composition.

The nail system is applied to nail(s) such that the order is nail/base coat (optional)/color coat of the invention/top coat (optional). During removal, the base coat is preferably peeled off from the edge of the nail/nail composition. Such removal of the nail composition is easy and quick (time efficient), and can be performed without the aid of solvent-based removers (although such removers can be used to aid in removal, if desired). The speed of removal of the nail composition can be increased by dipping nail(s) having an applied nail composition into warm water prior to peeling. "Warm water" is defined herein as water above room temperature such as, for example, water at 26° C.-60° C., preferably at 30° C.-50° C., including all ranges and subranges therebetween.

During application of the nail system, the base coat, if used, is applied first to the nail. Then, the color coat composition of the invention is applied to the base coat (if used); if base coat is not used, the color coat is applied to the nail. Then, if used, the top coat is applied to the color coat. In this manner, a nail composition comprising a base coat (optional), a color coat and a top coat (optional) can be prepared on a nail.

1. Base Coat (Optional)

In an embodiment a base coat is used in conjunction with a composition of the invention, in particular when the composition of the invention is a color coat. If present, the base coat can be any base coat commonly used and known to a person skilled in the art as being capable of being incorporated into a nail polish or varnish coloring set. Base coats provide adhesion of the color coat to the nail. In an embodiment the base coat in an easily removable water-based base coat. Preferred water-based base coats include UV-curable base coats as these offer greater adhesion to the nail.

In an embodiment according to the present invention, the base coat comprises (1) water and (2) at least one water-dispersed polymer. During use, the base coat helps the applied nail color composition of the invention to adhere to nails and also allows the applied color composition to be easily peeled off. In a particular embodiment the water-dispersed polymer (latex) used in the base coat is photo-curable. When a photo-curable latex is used, the base coat typically also includes a photo-initiator. Suitable photo-curable latexes include those described above as component (a). Suitable photo-initiators include those described above as component (c).

The photo-curable polymer is preferably present in the base coat in an amount from about 5% to about 35%, typically from about 10% to about 30%, more typically from about 15% to about 25%, most typically from about 17% to about 20%, based on the dry weight of the polymer, relative to the total weight of the composition, including all ranges and subranges in between.

Preferably, total water content present of the base coat is from about 46% to about 78%, more preferably from about 50% to about 73%, and more preferably from about 54% to about 67%, by weight, based on the total weight of the composition, including all ranges and subranges in between.

The photo-initiator is typically present in the base coat in an amount is ranging from about 0.2% to about 9%, typically from about 0.8% to about 2%, by weight relative to the weight of the composition, including all ranges and subranges therebetween.

In another embodiment, the base coat comprises (1) water and (2) at least one non-photo-curable latex. Such base coats are discussed, for example in Example 1 of WO2014/028021, which is herein incorporated by reference. In this embodiment, the non-photo-curable polymer is present in the base coat compositions (as measured in amounts of polymer solids content in the latex dispersion) generally ranging from about 5% to about 50%, typically from about 10% to about 45%, more typically from about 20% to about 40%, based on the total weight of the composition, including all ranges and subranges therebetween.

2. The Color Coat

The color coat in the nail composition system of the invention is a composition of the invention as described above comprising:

(a) from about 6% to about 20% by dry polymer weight of at least one photo-curable polymer dispersed in water;
(b) equal to or greater than about 10% by dry polymer weight of at least one non-photo-curable polymer dispersed in water;
(c) less than or equal to about 2% by weight of at least one photo-initiator;
(d) from about 0% to about 8% by weight of at least one plasticizer;
(e) from about 0.01% to about 10% by weight of a colorant;
(f) from about 40% to about 70% water;

wherein the ratio, by dry polymer weight, of the at least one photo-curable polymer (a) to the at least one non-photo-curable polymer (b) is from about 4:1 to about 1:5, and the sum, by dry polymer weight, of the photo-curable polymer (a) plus the non-photo-curable polymer (b) is from about 25% to about 40%; all weights being relative the total weight of the composition.

3. The Top Coat (Optional)

The inclusion of a top coat in the nail composition system of the invention is optional. If present, any top coat suitable for application to nails as a topcoat can be used.

In an embodiment according to the present invention, the top coat comprises (1) water and (2) at least one water-dispersed polymer. During use the top coat provides shine and/or protection to color coat. In an embodiment, the water-dispersed polymer (latex) used in the top coat is a photo-curable polymer. When a photo-curable polymer/latex is used, the top coat typically also includes a photo-initiator. Suitable photo-curable polymers/latexes include those described above as component (a). Suitable photo-initiators include those described above as component (c).

The photo-curable polymer is preferably present in the top coat in an amount of from about 5% to about 35%, typically from about 10% to about 30%, more typically from about 45% to about 25%, most typically about 17% to about 20%, based on the dry weight of the polymer, relative to the total weight of the composition, including all ranges and subranges in between.

Preferably, total water content present of the top coat is from about 46% to about 78%, more preferably from about 50% to about 73%, and more preferably from about 54% to about 67%, by weight, based on the total weight of the composition, including all ranges and subranges in between.

The photo-initiator is typically present in the top coat in an amount is ranging from about 0.2% to about 9%, typically from about 0.8% to about 2%, by weight relative to the weight of the composition, including all ranges and subranges therebetween.

In another embodiment, the top coat comprises (1) water and (2) at least one non-photo-curable polymer dispersed in water. Suitable non-photo-curable polymers/latexes are those described above for element (b). In this embodiment, the non-photo-curable polymer is present in the top coat compositions (as measured in amounts of polymer solids content in the latex dispersion) generally ranging from about 5% to about 45%, typically from about 10% to about 40%, more typically from about 20% to about 35%, relative to the total weight of the composition, including all ranges and subranges therebetween.

It is understood that the composition of the invention and the nail sets of the invention should be cosmetically or dermatologically acceptable, i.e. should contain non-toxic components and be physiologically acceptable. The compositions may be in any galenic form normally employed in the cosmetic and dermatological fields which is suitable for topical administration onto nails.

Methods of Making up Nails

In another embodiment, the present invention also provides methods of making up or protecting nails comprising applying to the nails at least one layer, preferably two, of a composition comprising:
  (a) from about 6% to about 20% by dry polymer weight of at least one photo-curable polymer dispersed in water;
  (b) equal to or greater than about 10% by dry polymer weight of at least one non-photo-curable polymer dispersed in water;
  (c) less than or equal to about 2% by weight of at least one photo-initiator;
  (d) from about 0% to about 8% by weight of at least one plasticizer;
  (e) from about 0.01% to about 10% by weight of a colorant;
  (f) from about 40% to about 70% water;
  wherein the ratio, by dry polymer weight, of the at least one photo-curable polymer (a) to the at least one non-photo-curable polymer (b) is from about 4:1 to about 1:5, and the sum, by dry polymer weight, of the photo-curable polymer (a) plus the non-photo-curable polymer (b) is from about 25% to about 40%; all weights being relative the total weight of the composition.

In another embodiment, the present invention also provides a method of making up or protecting nails comprising applying to the nails at least one base coat and at least one color coat as described above. In another embodiment, at top coat is also used.

"Making up" as used herein means to provide decoration (for example, color) to the nail.

"Protecting" as used herein means to inhibit damage to the nail (for example, chipping) by providing a protective layer on the nail.

In accordance with preferred embodiments of the preceding methods, the least one color coat according to the invention, and optionally the base and/or top coats, are applied topically to the nails of a person in an amount sufficient to achieve the desired result coloring and/or protecting the nails. The compositions may be applied to the desired area as needed.

In an embodiment, the invention also relates to a method of removing a nail composition comprising (1) one or more of a topcoat and a basecoat, and (2) at least one color coat according to the invention, wherein the method comprises removing the basecoat to effect removal of the basecoat as well as the color coat and topcoat (if present).

Nail Kits

In an embodiment present invention relates to a kit for making up nails containing a nail coloring composition according to the invention comprising:
  (a) from about 6% to about 20% by dry polymer weight of at least one photo-curable polymer dispersed in water;
  (b) equal to or greater than 10% by dry polymer weight of at least one non-photo-curable polymer dispersed in water;
  (c) less than or equal to about 2% by weight of at least one photo-initiator;
  (d) from about 0% to about 8% by weight of at least one plasticizer;
  (e) from about 0.01% to about 10% by weight of a colorant;
  (f) from about 40% to about 70% water;
  wherein the ratio, by dry polymer weight, of the at least one photo-curable polymer (a) to the at least one non-photo-curable polymer (b) is from about 4:1 to about 1:5, and the sum, by dry polymer weight, of the photo-curable polymer (a) to the non-photo-curable polymer (b) is from about 25% to about 40%; all weights being relative the total weight of the composition.

The kit optionally may include a base coat composition and/or a top coat composition. The kit may further comprise instructions for removing a nail composition by removing the basecoat to effect removal of all of the nail compositions.

The compositions according to the invention can be manufactured by known processes used generally in the cosmetics or dermatological field, including the processes described in the examples below.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention.

EXAMPLES

Example 1

Color Coats

The color coats according to the invention were prepared as follows:

A pigment paste was first made by adding triethanolamine to Syntran PC 5620 and mixing for 2 min in high speed mixer at 2750 rpm. Pigment(s), phenoxy ethanol and caprylyl glycol were then added to the preparation and mixed in a high speed mixer until the pigment(s) was well dispersed. The other ingredients were then added in a single pot process and mixed for 2 min in a high speed mixer at 2750 rpm.

For compositions that include parabens, the parabens were first dissolved in 0.2 g N-butyl ether propylene glycol, 0.8 dipropylene glycol dibenzoate and 1.7 g of tributyl citrate while heated at 60° C., prior to being added to the other ingredients.

TABLE 3

| INCI Name | Ex 1A* | Ex 1B* | Ex 1C | Ex 1D* | Ex 1E | Ex 1F* | Ex 1G | Ex 1H |
|---|---|---|---|---|---|---|---|---|
| 2,4,6-trimethylbenzoylphenyl phosphinate (c) (Lucirin TPO-L ™) | 1.7 | 1.7 | 1.7 | 1.7 | 1.7 | 1.7 | 1.7 | 1.7 |
| aliphatic, urethane/acrylic copolymer (a) (NeoRad ™ 465) | 21.5 | 0 | 14.7 | 0 | 14.7 | 0 | 14.7 | 17.0 |
| styrene/acrylates/ammonium/ methacrylate copolymer (and) sodium lauryl sulfate (and) sodium laureth sulfate (b) (Brand - Syntran PC 5620) | 6.0 | 6.0 | 6.0 | 6.0 | 6.0 | 31.1 | 15.8 | 10.7 |
| polyurethane-35 (b) (Baycusan ™ C1004) | 0 | 25.1 | 9.8 | 0 | 0 | 0 | 0 | 0 |
| acrylic styrene copolymer dispersion (b) (Neocryl ™ A1120) | 0 | 0 | 0 | 25.0 | 9.8 | 0 | 0 | |
| Acrylic styrene copolymer emulsion (b) (Neocryl ™ XK320) | | | | | | | | 6.8 |
| red 7 lake (e) | 4.4 | 4.4 | 4.4 | 4.4 | 4.4 | 4.4 | 4.4 | 4.4 |
| triethanolamine | 0.8 | 0.8 | 0.8 | 0.8 | 0.8 | 0.8 | 0.8 | 0.8 |
| phenoxy ethanol | 0.2 | 0.2 | 0.2 | 0.2 | 0.2 | 0.2 | 0.2 | 0.2 |
| caprylyl glycol | 0.2 | 0.2 | 0.2 | 0.2 | 0.2 | 0.2 | 0.2 | 0.2 |
| ethyl paraben | | | | | | | | 0.4 |
| methyl paraben | | | | | | | | 0.4 |
| PnB (N-butyl ether propylene glycol) | | | | | | | | 0.2 |
| dipropylene glycol dibenzoate (d) | | | | | | | | 0.8 |
| tributyl citrate (d) | | | | | | | | 1.7 |
| water (f) | 61.6 | 61.6 | 62.2 | 61.7 | 62.2 | 61.6 | 62.3 | 54.7 |
| Total | 100 | 100 | 100 | 100 | 100 | 100 | 100 | 100 |
| Polymer content (wt %) | 31.1 | 31.1 | 30.5 | 31.0 | 30.5 | 31.1 | 30.4 | 34.5 |
| UV curable polymer (dried latex):non-UV-curable (dried latex) | 4.2:1 | 0 | 1:1.11 | 0 | 1:1.11 | 0 | 1:1.11 | 1:1.03 |

*In Table 3 above, Examples 1A, B, D and F are comparative examples (e.g. no non-photo-curable latex and/or outside given ratio). Examples 1 C, E, G and H are compositions according to the invention.

In Example 1, two low Tg non-photo-curable latexes were used (Baycusan C1004, Tg=−47, and Neocryl A1120, Tg=−44) and one high Tg non-photo-curable latex was used (Syntran 5620, Tg=44). In each inventive composition of Examples 10, 1E, 1G and 1H the ratio of photo-curable polymer:non-photo-curable polymer is from 1:1.03 (=0.97) to 1:1.11 (=0.9).

Example 2

Nail System with Base and/or Top Coats and Color Coat

The compositions of the invention are preferably used as color coats for nails and may be used in a nail coloring system with any suitable base and/or top coat. In an embodiment, the base and/or top coats in such a system comprise at least one photo(UV)-curable latex and at least one photo initiator. In another embodiment the base and/or top coats in such a system comprise at least one non-photo-curable latex and a plasticizer. A non-limiting example of each of a suitable base coat and a suitable top coat are provided below.

Base Coat (Optional):

Water-based, non-photo-curable base coats are described in WO 2014/088570, herein incorporated by reference. An example of such base coat is Example 1 of WO 2014/088570, the composition for which is reproduced below in Table 4.

TABLE 4

Base Coat (optional): Water-Based, Non-photo-curable

| INCI Name | Wt (%) | Wt (%) (polymer in latex) | Wt (%) (polymer in composition) |
|---|---|---|---|
| styrene/acrylates/ammonium methacrylate copolymer (and) sodium lauryl sulfate (and) sodium lauryl sodium laureth sulfate (Brand: Syntran PC 5620) | 61 | 42 | 25.6 |
| ammonium acrylates copolymer | 22 | 40 | 8.8 |
| styrene/acrylates copolymer | 5.32 | 46 | 2.4 |
| polyurethane-34 | 2.85 | 32 | 0.9 |
| dipropylene glycol monobutyl ether | 1 | NA* | NA |
| propylene glycol dibenzoate | 4.59 | NA | NA |
| tributyl citrate | 1.24 | NA | NA |
| phenoxyethanol | 1 | NA | NA |
| Caprylyl glycol | 1 | NA | NA |
| Total film forming polymer(s) | | | 37.7 |

*NA = Not applicable.

Color Coat:

Any photo-curable color coat according to the invention can be used.

Top Coat (Optional):

Any top coat comprising a photo-curable-curable, water-dispersed polymer may be used. An example of a suitable top cop is provided below in Table 5.

TABLE 5

Top Coat (Optional) - Water-based, Photo-Curable

| Code | INCI | % |
| --- | --- | --- |
| photoinitiator | 2,4,6-trimethylbenzoylphenyl phosphinate (Brand: Lucirin TPO-L) | 2 |
| photo (UV)- curable latex | aliphatic urethane acrylic copolymer (Brand: NeoRad R-440) | 17.5 |
| photo (UV) -curable latex | urethane acrylate dispersion (Brand: Bayhydrol UV XP 2775) | 18.2 |
| | water | 62.3 |
| | total | 100 |
| | polymer content (weight %) | 35.7 |

The top and base coats above were prepared as follows:

All ingredients were combined in one pot and stirred for 3 minutes in a high speed mixer at 2750 rpm.

Assessment of Performance of Test Compositions

The compositions of the invention were assessed for various parameters and compared to comparative and benchmark compositions. The protocols for the various tests are as follows.

Adhesion Test:

Adhesion assessment was carried out by applying test compositions on a prototype nail, Vitro-Nail®, which is commercially available from IMS Inc. Test compositions were applied to the Vitro-Nail® using a 6 mil draw down bar. Water based color coat compositions were first air dried then cured for 60 seconds with an OPI LED lamp.

For the full set systems, the adhesion was measured after all three compositions (base coat, color coats, and top coat) were applied.

For the color coat only compositions, the adhesion was assessed after application of the second coat. Adhesion was assessed using the cross hatch test described above in the definition section. In this test, adhesion is graded following an ASTM (American Society of Testing Materials international standards) table as follows:

| Classification | Percent area removed |
| --- | --- |
| 5B | 0%-None |
| 4B | Less than 5% |
| 3B | 5-15% |
| 2B | 15-35% |
| 1B | 35-65% |
| 0B | Greater than 65% |

For Vitro-Nails® treated with only 2 color coats (2 coats of the same composition), the samples were immersed for 1 minute in acetone and then swapped once with a Q-tip. The appearance of the Vitro-Nail® nail was then photographed and recorded.

Soapy Water Resistance at 45° C. Test:

Nail spoons (commercially available from Daret Inc) coated with test nail compositions were immersed for 20 minutes in a soapy water medium at 45° C. The appearance of the film was graded from 0 to 5, wherein 5 means a very good appearance and 0 is a very bad appearance.

Impact Resistance Test:

Impact testing measures the minimum amount of energy necessary to cause failure of a test composition (e.g cracking of film). For each test composition films were prepared on 5 different steel plates (6 mil draw down bar, air dried and then 60 s cure under OPI LED lamp). A film area was only impacted once. Each test composition was impacted until there was a failure (film cracked).

Impact Resistance was Measured with a Heavy Duty Impact Tester from BYK Gardner.

The impact energy of this system depends on the weight and the height from which the weight is dropped. Higher the weight and height from which the weight is dropped, higher is the impact energy. The impact resistance values are given in kg.cm and correspond to the lowest (weight×height) for which the specimen shows failure.

Shine Test:

Each test composition was deposited on black/white Leneta paint test cards as follows: Emil draw down film was applied, allowed to air dry and then cured for 60 seconds under an OPI LED lamp. The shine of each of the films formed with the test compositions was then measured using a Micro-Tri-Gloss 20/60/85 degree gloss meter from BYK Gardner.

In this test, "high shine" (or high gloss) means a reading of >70GU at a 60° angle.

Tackiness Test:

The tackiness of compositions applied to Vitro-Nails® was assessed by wiping the Vitro-Nail® with a Q-tip, once, as previously described.

The measurement criteria for this test are as follows:

| Tackiness Scale Black/White Paper | | |
| --- | --- | --- |
| Not tacky | 5 | Q tip slides with no effect on surface |
| | 4 | Q tip slightly marks + slight tackiness |
| | 3 | tacky with no loss of cotton fibers |
| | 2 | A few fibers of cotton stick to the film |
| Very tacky | 1 | (a lot of cotton from Q tip sticks to film) |

Evaluation of Inventive Color Compositions—2 Coat Application

The inventive color composition of Ex 1H was compared with a full set nail system (base coat, color coast, and top coat), as well as with just the color compositions, of two commercial nail products (Commercial 1 and Commercial 2). In each case, two color coats were applied. The results of this comparison are shown in Table 6 below.

TABLE 6

| | | Commercial 1* | | Commercial 2* | | Inventive Composition of Ex. 1H |
| --- | --- | --- | --- | --- | --- | --- |
| | | Full set | 2 color layers | Full set | 2 color layers | 2 color layers |
| Application | | Need IPA Wipe after application Base coat 10 s 2 Color 2 × | No IPA Wipe after application 2 Color coat 2 × 2 min | Need IPA Wipe after application Base coat 30 s 2 Color 2 × | No IPA Wipe after application 2 Color 2 × 30 s | No IPA Wipe after application 2 Color 2 × 60 s |

TABLE 6-continued

|  | Commercial 1* | | Commercial 2* | | Inventive Composition of Ex. 1H |
|---|---|---|---|---|---|
|  | Full set | 2 color layers | Full set | 2 color layers | 2 color layers |
|  | 2 min Top coat 2 min | | 30 s Top coat 1 min | | |
| Adhesion (no buffering) | 0 | 0 | 0 | 0 | 4 |
| Acetone Removal | No transfer to Q-tip swipe; surface completely untouched | Slight transfer to Q-tip swipe; film started curling off of Vitro-Nail ® | No transfer to Q-tip swipe; surface completely untouched | Slight transfer to Q-tip swipe; very little removal | Partial transfer to Q-tip swipe |
| Tackiness After 24 hours | 5 | 1 | 5 | 1 | 5 |
| Shine | high | tacky non measureable | high | tacky non measureable | high |

*Commercial 1 and Commercial 2 are solvent-based, not aqueous, UV-curable compositions comprising acrylate monomers/oligomers film formers.

In each of the above protocols, 1 is very bad and 5 is very good.

As shown in Table 6, the water-based color coat of the invention had good adhesion, easy removal with acetone, was not tacky and had comparative shine relative to the solvent-based commercial comparators.

Evaluation of Color Films that Include Higher Amounts of Non-Photo-Curable Latexes Low Tg Latexes: The performance of inventive color compositions of Ex. 10 and Ex. 1E was compared with the performance of comparative compositions of Exs 1A, 1B and 1 D. The results of this assessment are provided below in Table 7A. Following the same protocols, a full set (base coat, 2 color coats, top coat) of Commercial 1 was also assessed. The results of this assessment are provided below in Table 7B.

TABLE 7A

|  | Comparative FLAs (2 color coats) | | | Invention examples (2 color coats) | |
|---|---|---|---|---|---|
| Properties | Ex 1 A | Ex 1 B | Ex 1 D | Ex 1 C | Ex 1 E |
| Need of IPA wipe after curing | no | no | no | no | no |
| Shine and film appearance | High | High | High | High | High |
| Impact resistance (kg · cm) | 25 | >200 | >200 | 140-160 | 40-50 |
| Soapy-water resistance at 45° C. | 4 | 1 | 2 | 5 | 4 |
| Acetone removal 1 min immersion followed by Q-tip swipe | Slight transfer to Q-tip swipe (very little removal) | Complete transfer to Q-tip swipe (complete removal) | Partial transfer to Q-tip swipe (some removal) | Complete transfer to Q-tip swipe (complete removal) | Complete transfer to Q-tip swipe (complete removal) |

TABLE 7B

| Properties | Commercial 1-Full Set |
|---|---|
| Need of IPA wipe after curing | yes |
| Shine and film appearance | High |
| Impact resistance (kg · cm) | 160 |
| Soapy-water resistance at 45° C. | 5 |
| Acetone removal 1 min immersion followed by Q-tip swipe | Film not modified. No transfer to Q-tip swipe (no removal) |

As is shown above in Table 7A, the inventive compositions comprising higher amounts of low Tg non-UV-curable latex have improved mechanical properties (increased impact resistance), warm soapy water resistance, and are more easily removed by acetone compared to the comparative formulas (Exs. 1A, 1B and 1D). These properties were also shown in contrast to Commercial 1 (Table 7B).

High Tg Latexes: The performance of inventive color composition Ex. 1G was compared with the performance of comparative compositions of Exs 1A and 1F. The results of this assessment are provided below in Table 8A.

Following the same protocols, a full set (base coat, 2 color coats, top coat) of Commercial 1 was also assessed. The results of this assessment are provided below in Table 8B.

TABLE 8A

| Properties | Comparative Exs | | Invention Example |
|---|---|---|---|
| FLA | Ex 1A | Ex 1F | Ex 1G |
| Need of IPA wipe after curing | no | no | no |
| Shine and film appearances | high | Low (no film formation) | high |
| Impact resistance (kg · cm) | 25 | N/A | 20 |
| Soapy-water resistance at 45° C. | 4 | 0 | 4 |
| Acetone removal 1 min immersion followed by Q-tip swipe | Slight transfer to Q-tip swipe (very little removal) | Complete transfer to Q-tip swipe (complete removal) | Complete transfer to Q-tip swipe (complete removal) |
| Adhesion cross cut test | 4B | 0B | 4B |

TABLE 8B

| Properties | Commercial 1 |
|---|---|
| Need of IPA wipe after curing | yes |
| Shine and film appearances | high |
| Impact resistance (kg · cm) | 160 |
| Soapy-water resistance at 45° C. | 5 |
| Acetone removal 1 min immersion followed by Q-tip swipe | Film not modified. No transfer to Q-tip swipe (no removal) |
| Adhesion cross cut test | 3B |

As is shown in Table 8A, the composition of the invention comprising a high Tg non-photo-curable latex and a photo-curable latex (Ex. 1G) has good film forming properties, good adhesion, and at least equal to or improved acetone removal and warm soapy water resistance compared to Comparative Examples 1A and 1F. These properties were also shown in contrast to Commercial 1 (Table 8B).

Composition Including Plasticizers:

The performance of an inventive color composition comprising plasticizers (Ex 1H) was compared with the performance of comparative composition of Ex 1A. The results of this assessment are provided below in Table 9A.

Following the same protocols, a full set (base coat, 2 color coats, top coat) of Commercial 1 was also assessed. The results of this assessment are provided below in Table 9B.

TABLE 9A

| Properties | Comparative Ex 1A | Inventive Ex. 1H |
|---|---|---|
| Tackiness after cure | No | No |
| Need of IPA wipe | No | No |
| Shine and film appearance | High | High |
| Impact resistance (kg · cm) | 45 | 70 |
| Cross hatch | 4B | 3B |
| Soapy-water resistance at 45° C. | 2 | 5 |

TABLE 9B

| Properties | Commercial 1 |
|---|---|
| Tackiness after cure | Yes |
| Need of IPA wipe | Yes |
| Shine and film appearance | High |
| Impact resistance (kg · cm) | 160 |
| Acetone removal 1 min immersion followed by Q-tip swipe | Film not modified. No transfer to Q-tip swipe (no removal) |
| Cross hatch | 3B |

As is shown in Table 9A, inventive compositions comprising a plasticizer retain better mechanical properties and have good adhesion and shine relative to a comparative composition devoid of plasticizer.

As is shown in Table 9B, the inventive composition containing a plasticizer has good properties also in comparison to the commercial benchmark Commercial 1.

What is claimed is:

1. A cosmetic composition for application to the nails comprising:
    (a) from about 6% to about 20%, by dry weight, of at least one photo-curable polymer dispersed in water;
    (b) from about 10% to about 30%, by dry weight, of at least one non-photo-curable polymer dispersed in water;
    (c) less than or equal to about 2% by weight of at least one photo-initiator;
    (d) from about 0% to about 8% by weight of at least one plasticizer;
    (e) optionally a colorant; and
    (f) from about 40% to about 70% water;
    wherein the ratio, by dry polymer weight, of the at least one photo-curable polymer (a) to the at least one non-photo-curable polymer (b) is from about 4:1 to about 1:5, and the sum, by dry polymer weight percent, of the photo-curable polymer (a) plus the non-photo-curable polymer (b) is from about 25% to about 40%; all weights being relative the total weight of the composition, wherein the at least one non-photo-curable polymer dispersed in water (b) has at least one low glass transition temperature (Tg), wherein the photo-curable polymer dispersed in water (a) has a number average molecular weight from about 10,100 Mn to about 500,000 Mn, and wherein the photo-curable polymer dispersed in water (a) is selected from an aliphatic urethane acrylic copolymer, an aliphatic anionic polyurethane dispersion, an aromatic polyurethane dispersion, and mixtures thereof.

2. The composition of claim 1 comprising from about 0.001% to about 10%, by weight, of at least one colorant.

3. The composition of claim 2 wherein the at least one photo-curable polymer dispersed in water (a) is a polyurethane acrylate polymer.

4. The composition of claim 3 wherein the at least one non-photo-curable polymer that is dispersed in water (b) is selected from polyurethanes, styrene acrylic copolymers, and mixtures thereof.

5. The composition of claim 4 wherein the photo-initiator (c) is present in an amount of from about 0.5% to about 2%.

6. The composition of claim 5 wherein the photo-initiator (c) has a wavelength greater than about 200 nm.

7. The composition of claim 6 wherein the photo-initiator (c) is 2,4,6-(trimethylbenzoyl)-phenyl phosphinate.

8. The composition of claim 2 comprising 0% plasticizer (d).

9. The composition of claim 5 wherein a plasticizer (d) present in an amount of from about 1% to about 2.5%.

10. The composition of claim 9 wherein the plasticizer (d) is selected from dipropylene glycol dibenzoate, tributyl citrate, and mixtures thereof.

11. The composition of claim 9 wherein the water (f) is present in an amount of from about 50% to about 68%.

12. The composition of claim 1 wherein the non-photo-curable polymer dispersed in water (b) is selected from polyurethane-35, styrene/acrylates/ammonium methacrylate copolymer, acrylic/styrene copolymer, and mixtures thereof.

13. A cosmetic composition for application to the nails comprising:
  (a) from about 6% to about 20%, by dry polymer weight, of at least one photo-curable polymer latex;
  (b) from about 10% to about 30%, by dry polymer weight, of at least one polyurethane non-photo-curable latex;
  (c) less than or equal to about 2% by weight of at least one photo-initiator;
  (d) from about 0% to about 8% by weight of at least one plasticizer;
  (e) optionally a colorant; and
  (f) from about 40% to about 70% water;
  wherein the ratio, by dry polymer weight, of the polymer in the at least one photo-curable latex (a) to the polymer in the at least one non-photo-curable latex (b) is from 4:1 to 1:5, and the sum, by dry polymer weight percent, of the polymer in the photo-curable latex and the polymer in the non-photo-curable latex (b) is from about 25% to about 40%; all weights being relative the total weight of the composition, wherein the at least one non-photo-curable polymer dispersed in water (b) has at least one low glass transition temperature (Tg), wherein the photo-curable polymer dispersed in water (a) has a number average molecular weight from about 10,100 Mn to about 500,000 Mn, and wherein the photo-curable polymer dispersed in water (a) is selected from an aliphatic urethane acrylic copolymer, an aliphatic anionic polyurethane dispersion, an aromatic polyurethane dispersion, and mixtures thereof.

14. A system for coloring nails comprising:
  (1) at least one base coat composition comprising at least one polymer-in-water dispersion;
  (2) at least one color coat composition comprising:
  (a) from about 6% to about 20%, by dry weight, of at least one photo-curable polymer dispersed in water;
  (b) from about 10% to about 30%, by dry weight, of at least one non-photo-curable polymer dispersed in water;
  (c) less than or equal to about 2% by weight of at least one photo-initiator;
  (d) from about 0% to about 8% by weight of at least one plasticizer;
  (e) optionally a colorant; and
  (f) from about 40% to about 70% water;
  wherein the ratio, by dry polymer weight, of the at least one photo-curable polymer (a) to the at least one non-photo-curable polymer (b) is from 4:1 to 1:5, and the sum, by dry polymer weight percent, of the photo-curable polymer (a) plus the non-photo-curable polymer (b) is from about 25% to about 40%; all weights being relative the total weight of the composition; and
  (3) at least one top coat composition comprising at least one polymer-in-water dispersion, wherein the at least one non-photo-curable polymer dispersed in water (b) has at least one low glass transition temperature (Tg), wherein the photo-curable polymer dispersed in water (a) has a number average molecular weight from about 10,100 Mn to about 500,000 Mn, and wherein the photo-curable polymer dispersed in water (a) is selected from an aliphatic urethane acrylic copolymer, an aliphatic anionic polyurethane dispersion, an aromatic polyurethane dispersion, and mixtures thereof.

15. A kit for coloring nails comprising
  (1) at least one base coat composition comprising at least one polymer-in-water dispersion;
  (2) at least one color coat composition comprising:
  (a) from about 6% to about 20%, by dry weight, of at least one photo-curable polymer dispersed in water;
  (b) from about 10% to about 30%, by dry weight, of at least one non-photo-curable polymer dispersed in water;
  (c) less than or equal to about 2% by weight of at least one photo-initiator;
  (d) from about 0% to about 8% by weight of at least one plasticizer;
  (e) optionally a colorant; and
  (f) from about 40% to about 70% water;
  wherein the ratio, by dry polymer weight, of the at least one photo-curable polymer (a) to the at least one non-photo-curable polymer (b) is from 4:1 to 1:5, and the sum, by dry polymer weight percent, of the photo-curable polymer (a) plus the non-photo-curable polymer (b) is from about 25% to about 40%; all weights being relative the total weight of the composition; and
  (3) at least one top coat composition comprising at least one polymer-in-water dispersion, wherein the at least one non-photo-curable polymer dispersed in water (b) has at least one low glass transition temperature (Tg), wherein the photo-curable polymer dispersed in water (a) has a number average molecular weight from about 10,100 Mn to about 500,000 Mn, and wherein the photo-curable polymer dispersed in water (a) is selected from an aliphatic urethane acrylic copolymer, an aliphatic anionic polyurethane dispersion, an aromatic polyurethane dispersion, and mixtures thereof.

16. A method of coloring nails comprising applying to the nails a composition comprising:
  (a) from about 6% to about 20%, by dry weight, of at least one photo-curable polymer dispersed in water;
  (b) from about 10% to about 30%, by dry weight, of at least one non-photo-curable polymer dispersed in water;
  (c) less than or equal to about 2% by weight of at least one photo-initiator;
  (d) from about 0% to about 8% by weight of at least one plasticizer;
  (e) optionally a colorant; and
  (f) from about 40% to about 70% water;
  wherein the ratio, by dry polymer weight, of the at least one photo-curable polymer (a) to the at least one non-photo-curable polymer (b) is from 4:1 to 1:5, and the sum, by dry polymer weight percent, of the photo-curable polymer (a) plus the non-photo-curable polymer (b) is from about 25% to about 40%; all weights being relative the total weight of the composition, wherein the at least one non-photo-curable polymer dispersed in water (b) has at least one low glass transition temperature (Tg), wherein the photo-curable polymer dispersed in water (a) has a number average molecular weight from about 10,100 Mn to about 500,000 Mn, and wherein the photo-curable polymer dispersed in water (a) is selected from an aliphatic urethane acrylic copolymer, an aliphatic anionic polyurethane dispersion, an aromatic polyurethane dispersion, and mixtures thereof.

17. A method of making a cosmetic composition for application to the nails comprising:
(1) combining
(a) from about 6% to about 20%, by dry weight, of at least one photo-curable polymer dispersed in water;
(b) from about 10% to about 30%, by dry weight, of at least one non-photo-curable polymer dispersed in water;
(c) less than or equal to about 2% by weight of at least one photo-initiator;
(d) from about 0% to about 8% by weight of at least one plasticizer;
(e) optionally a colorant; and
(f) from about 40% to about 70% water;
wherein the ratio, by dry polymer weight, of the at least one photo-curable polymer (a) to the at least one non-photo-curable polymer (b) is from 4:1 to 1:5, and the sum, by dry polymer weight percent, of the photo-curable polymer (a) plus the non-photo-curable polymer (b) is from about 25% to about 40%; all weights being relative the total weight of the composition; and (2) mixing the foregoing components until uniformly distributed, wherein the at least one non-photo-curable polymer dispersed in water (b) has at least one low glass transition temperature (Tg), wherein the photo-curable polymer dispersed in water (a) has a number average molecular weight from about 10,100 Mn to about 500,000 Mn, and wherein the photo-curable polymer dispersed in water (a) is selected from an aliphatic urethane acrylic copolymer, an aliphatic anionic polyurethane dispersion, an aromatic polyurethane dispersion, and mixtures thereof.

* * * * *